US 11,497,545 B2

(12) United States Patent
Sims et al.

(10) Patent No.: US 11,497,545 B2
(45) Date of Patent: Nov. 15, 2022

(54) ELECTROSURGICAL FORCEPS

(71) Applicant: COVIDIEN LP, Mansfield, MA (US)

(72) Inventors: Grant T. Sims, Boulder, CO (US);
Kelley D. Goodman, Erie, CO (US);
Craig V. Krastins, Arvada, CO (US);
Robert F. McCullough, Jr., Boulder, CO (US); Jennifer L. Rich, Parker, CO (US); Daniel W. Mercier, Erie, CO (US)

(73) Assignee: Covidien LP, Mansfield, MA (US)

(*) Notice: Subject to any disclaimer, the term of this patent is extended or adjusted under 35 U.S.C. 154(b) by 835 days.

(21) Appl. No.: 16/276,072

(22) Filed: Feb. 14, 2019

(65) Prior Publication Data
US 2020/0261146 A1 Aug. 20, 2020

(51) Int. Cl.
*A61B 18/14* (2006.01)
*A61B 18/00* (2006.01)

(52) U.S. Cl.
CPC .............. *A61B 18/1442* (2013.01); *A61B 2018/00916* (2013.01); *A61B 2018/1455* (2013.01)

(58) Field of Classification Search
CPC . A61B 18/14; A61B 18/1442; A61B 18/1445; A61B 18/1448; A61B 2018/0063; A61B 2018/00916; A61B 2018/1455
USPC .............. 606/51–52, 169, 205–207
See application file for complete search history.

(56) References Cited

U.S. PATENT DOCUMENTS

| | | |
|---|---|---|
| 5,219,354 A | 6/1993 | Choudhury et al. |
| 5,447,265 A | 9/1995 | Vidal et al. |
| 5,499,997 A | 3/1996 | Sharpe et al. |
| 5,797,938 A | 8/1998 | Paraschac et al. |
| 5,860,975 A | 1/1999 | Goble et al. |
| 6,603,100 B2 | 8/2003 | Wilkins et al. |
| 7,207,472 B2 | 4/2007 | Wukusick et al. |
| 7,297,136 B2 | 11/2007 | Wyrick |
| 7,550,975 B2 | 6/2009 | Honda et al. |
| 7,819,299 B2 | 10/2010 | Shelton, IV et al. |
| 8,197,479 B2 | 6/2012 | Olson et al. |
| 8,343,151 B2 | 1/2013 | Siebrecht et al. |
| 8,388,646 B2 | 3/2013 | Chojin |
| 8,480,671 B2 | 7/2013 | Mueller |
| 8,568,412 B2 | 10/2013 | Brandt et al. |
| 8,628,557 B2 | 1/2014 | Collings et al. |
| 8,679,115 B2 | 3/2014 | Reschke |
| 8,696,665 B2 | 4/2014 | Hunt et al. |
| 8,752,264 B2 | 6/2014 | Ackley et al. |
| 8,920,461 B2 | 12/2014 | Unger et al. |
| 8,968,313 B2 | 3/2015 | Larson |
| 8,973,805 B2 | 3/2015 | Scirica et al. |
| 9,345,534 B2 | 5/2016 | Artale et al. |
| 9,610,114 B2 | 4/2017 | Baxter, III et al. |
| 9,675,405 B2 | 6/2017 | Trees et al. |

(Continued)

FOREIGN PATENT DOCUMENTS

| | | |
|---|---|---|
| DE | 102010013060 A1 | 9/2011 |
| DE | 202012013219 U1 | 11/2015 |
| WO | 2009153015 A1 | 12/2009 |

*Primary Examiner* — Khadijeh A Vahdat (57) ABSTRACT

An end effector of an electrosurgical forceps includes a first jaw member, a second jaw member, and a cap. The first jaw member has a pivot pin extending inwardly from an inner lateral side thereof. The second jaw member is pivotably coupled to the pivot pin. The cap couples the first and second jaw members to one another.

9 Claims, 5 Drawing Sheets

(56) References Cited

U.S. PATENT DOCUMENTS

| | | | |
|---|---|---|---|
| 9,707,029 B2 | 7/2017 | Nobis et al. | |
| 9,877,775 B2 | 1/2018 | Hart | |
| 2001/0045442 A1 | 11/2001 | Whitman | |
| 2003/0018331 A1* | 1/2003 | Dycus | A61B 18/085 606/48 |
| 2004/0094597 A1 | 5/2004 | Whitman et al. | |
| 2007/0043352 A1 | 2/2007 | Garrison et al. | |
| 2007/0173814 A1 | 7/2007 | Hixson et al. | |
| 2010/0286691 A1 | 11/2010 | Kerr et al. | |
| 2011/0054468 A1 | 3/2011 | Dycus | |
| 2012/0197253 A1 | 8/2012 | Nishimura et al. | |
| 2012/0265241 A1 | 10/2012 | Hart et al. | |
| 2013/0138101 A1* | 5/2013 | Kerr | A61B 18/1442 606/45 |
| 2013/0296843 A1 | 11/2013 | Boudreaux et al. | |
| 2014/0005704 A1 | 1/2014 | Vakharia et al. | |
| 2014/0276738 A1 | 9/2014 | Price et al. | |
| 2014/0276970 A1 | 9/2014 | Messerly et al. | |
| 2014/0309665 A1 | 10/2014 | Parihar et al. | |
| 2015/0272660 A1 | 10/2015 | Boudreaux et al. | |
| 2016/0135868 A1 | 5/2016 | Joseph et al. | |
| 2016/0166256 A1 | 6/2016 | Baxter, III et al. | |
| 2017/0196629 A1 | 7/2017 | Nagtegaal | |
| 2017/0238991 A1 | 8/2017 | Worrell et al. | |
| 2017/0245933 A1 | 8/2017 | Graham et al. | |
| 2017/0367752 A1 | 12/2017 | Boudreaux et al. | |

* cited by examiner

ELECTROSURGICAL FORCEPS

BACKGROUND

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

As used herein, the terms parallel and perpendicular are understood to include relative configurations that are substantially parallel and substantially perpendicular up to about +/−10 degrees from true parallel and true perpendicular.

An end effector of an electrosurgical forceps provided in accordance with aspects of the present disclosure includes first and second jaw members and a cap for coupling the first and second jaw members. Each of the first and second jaw members includes a jaw body and a proximal body portion extending proximally from the jaw body. The proximal body portion of the first jaw member has an inner lateral side and a pivot pin extending inwardly from the inner lateral side. The proximal body portion of the second jaw member is pivotably coupled to the pivot pin and has an inner lateral side adjacent the inner lateral side of the first jaw member. The cap is fixed to the inner lateral side of the proximal body portion of the first jaw member.

In aspects, the pivot pin may define a slot having a portion of the cap received therein.

In some aspects, the cap may have a proximal end portion and a distal end portion. The proximal and distal end portions of the cap may be fixed to the proximal body portion of the first jaw member.

In further aspects, the cap may have an intermediate portion received in the slot of the pivot pin.

In other aspects, the proximal body portion of the second jaw member may define a recessed cavity configured to receive the cap therein.

In aspects, the proximal body portion of the second jaw member may have an inner surface disposed in the recessed cavity. The cap may be disposed over and in contact with the inner surface.

In some aspects, the proximal body portion of the second jaw member may define an opening extending laterally therethrough. The proximal body portion of the first jaw member may have a protuberance projecting from the inner lateral side thereof and through the opening. The cap may have a distal end portion fixed to the protuberance.

In further aspects, the pivot pin may be fixed relative to the proximal body portion of the first jaw member.

In other aspects, the cap may be welded at the proximal and distal end portions to the inner lateral side of the first jaw member.

In aspects, the cap may be spaced laterally from the inner lateral side of the first jaw member to define a gap between the cap and the inner lateral side of the first jaw member. The gap may be configured to receive the proximal body portion of the second jaw member therein.

In accordance with another aspect of the present disclosure, an end effector of an electrosurgical forceps is provided and includes first and second jaw members, a pivot pin, and a cap. Each of the first and second jaw members includes a jaw body and a proximal body portion extending proximally from the jaw body. The pivot pin has a first end rotationally supported in the proximal body portion of the first jaw member. The proximal body portion of each of the first and second jaw members has an inner lateral side disposed adjacent one another. The cap is attached to the proximal body portion of the second jaw member and the second end of the pivot pin. The pivot pin and the cap are configured to pivotably couple the first and second jaw members to one another.

In aspects, the proximal body portion of the second jaw member may define a cavity configured to receive the cap therein.

In some aspects, the pivot pin may be fixed relative to the proximal body portion of the second jaw member and the cap.

In further aspects, the cap may be rotatably engaged to the first jaw member.

In other aspects, the cap may be welded to the proximal body portion of the second jaw member and the pivot pin.

In aspects, the cap may be spaced laterally from the inner lateral side of the first jaw member to define a gap between the cap and the inner lateral side of the first jaw member. The gap may be configured to receive the proximal body portion of the second jaw member therein.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
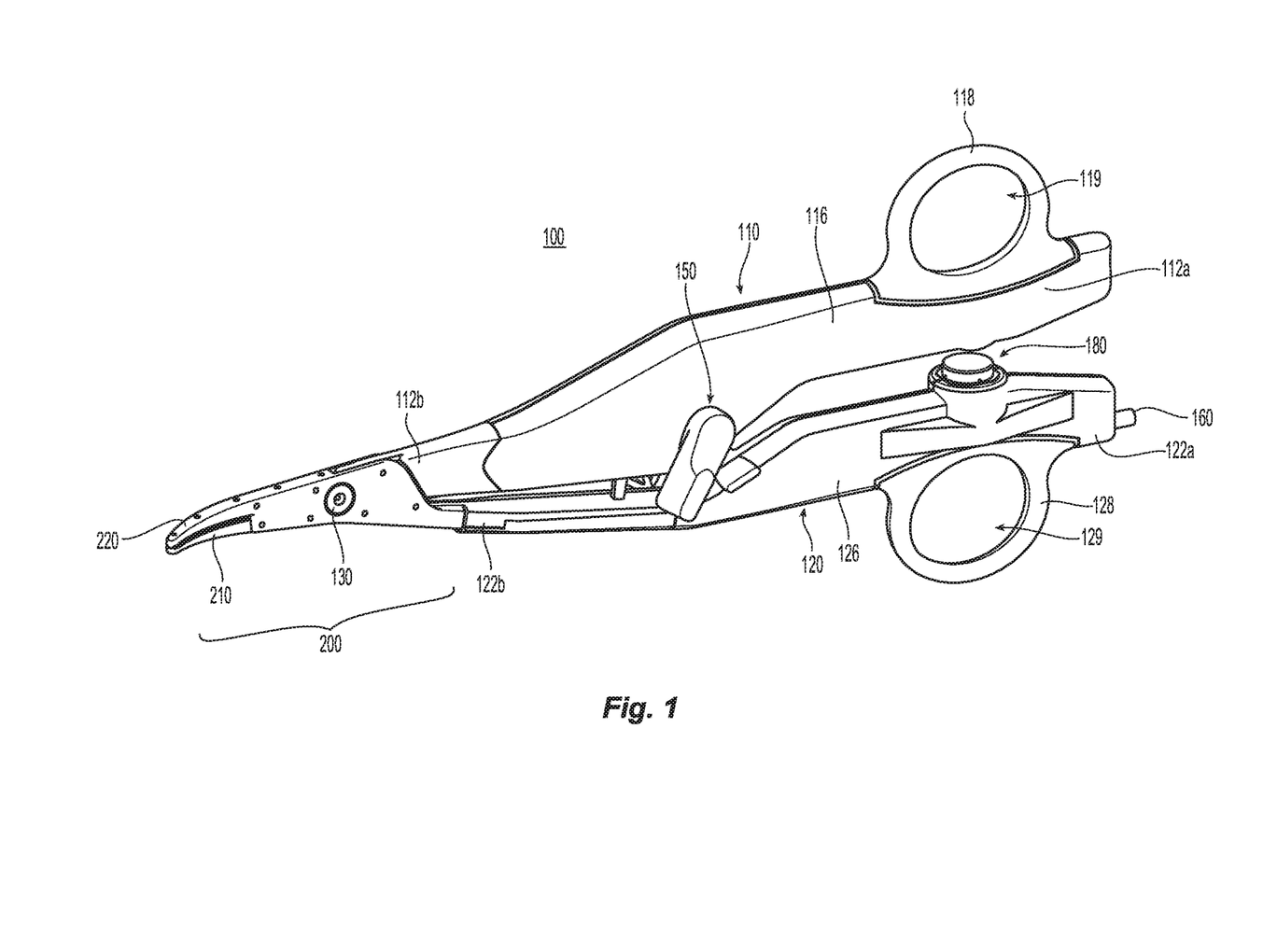
FIG. 1 is a side, perspective view of an electrosurgical forceps including an end effector provided in accordance with aspects of the present disclosure.
Figure 2:
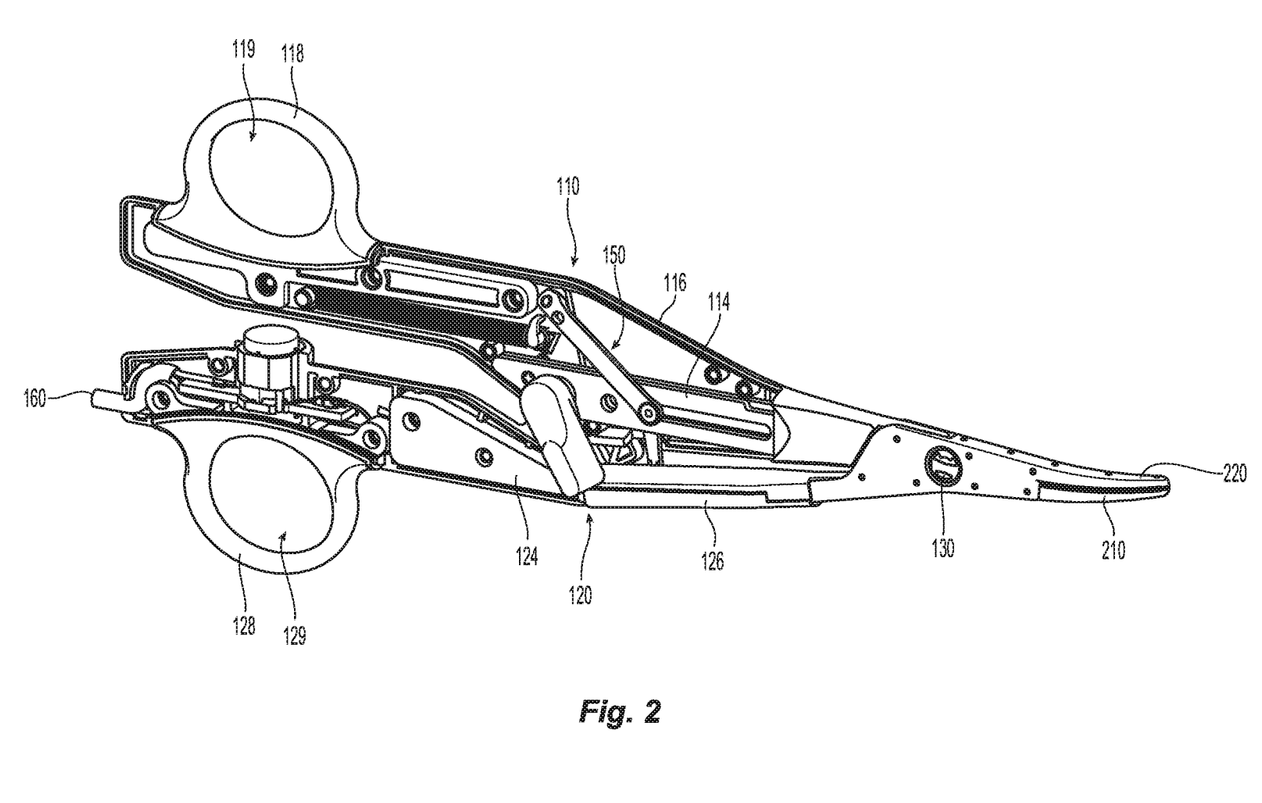
FIG. 2 is a perspective view from one side of the forceps of FIG. 1 with portions of outer housings of first and second shaft members removed to illustrate the internal components therein.

Referring to FIGS. 1 and 2, a forceps 100 provided in accordance with the present disclosure generally includes first and second shaft members 110, 120 and an end effector 200. Shaft members 110, 120 each have a respective proximal end portion 112a, 122a and a respective distal end portion 112b, 122b. End effector 200 includes first and second jaw members 210, 220 extending from distal end portions 112b, 122b of first and second shaft members 110, 120, respectively. Forceps 100 further includes a pivot member 130 pivotably coupling first and second shaft members 110, 120 with one another, a knife (not explicitly shown), a knife deployment mechanism 150 for selectively deploying the knife, and a switch assembly 180 for enabling the selective supply of electrosurgical energy to end effector 200. An electrosurgical cable 160 electrically couples forceps 100 to a source of energy (not shown), e.g., an electrosurgical generator, to enable the supply of electrosurgical energy to jaw members 210, 220 of end effector 200 upon activation of switch assembly 180.

Each shaft member 110, 120 includes an inner frame 114, 124, an outer housing 116, 126 surrounding at least a portion of the respective inner frame 114, 124, and a handle 118, 128 engaged with the respective outer housing 116, 126 towards proximal end portions 112a, 122a of first and second shaft members 110, 120, respectively. Inner frame 124 of second shaft member 120 and inner frame 114 of first shaft member 110 are pivotably coupled to one another via pivot member 130 such that shaft members 110, 120 are movable relative to one another between spaced-apart and approximated positions to pivot jaw members 210, 220 relative to one another between open and closed positions. In some aspects, jaw members 210, 220 are pivotably coupled to one another via pivot member 130.

Outer housings 116, 126 of first and second shaft members 110, 120 enclose and/or operably support the internal components disposed within first and second shaft members 110, 120. More specifically, outer housing 116 of first shaft member 110 encloses and supports at least a portion of inner frame 114 and the knife deployment mechanism 150, while outer housing 126 of shaft member 120 receives electrosurgical cable 160 and encloses and supports at least a portion of inner frame 124, switch assembly 180, and lead wires of electrosurgical cable 160. Handles 118, 128 are engaged with outer housings 116, 126 towards proximal end portions 112a, 112b of first and second shaft members 110, 120 and extend outwardly from first and second shaft members 110, 120. Handles 118, 128 define finger holes 119, 129 configured to facilitate grasping and manipulating shaft members 110, 120.

Figures 3, 4:
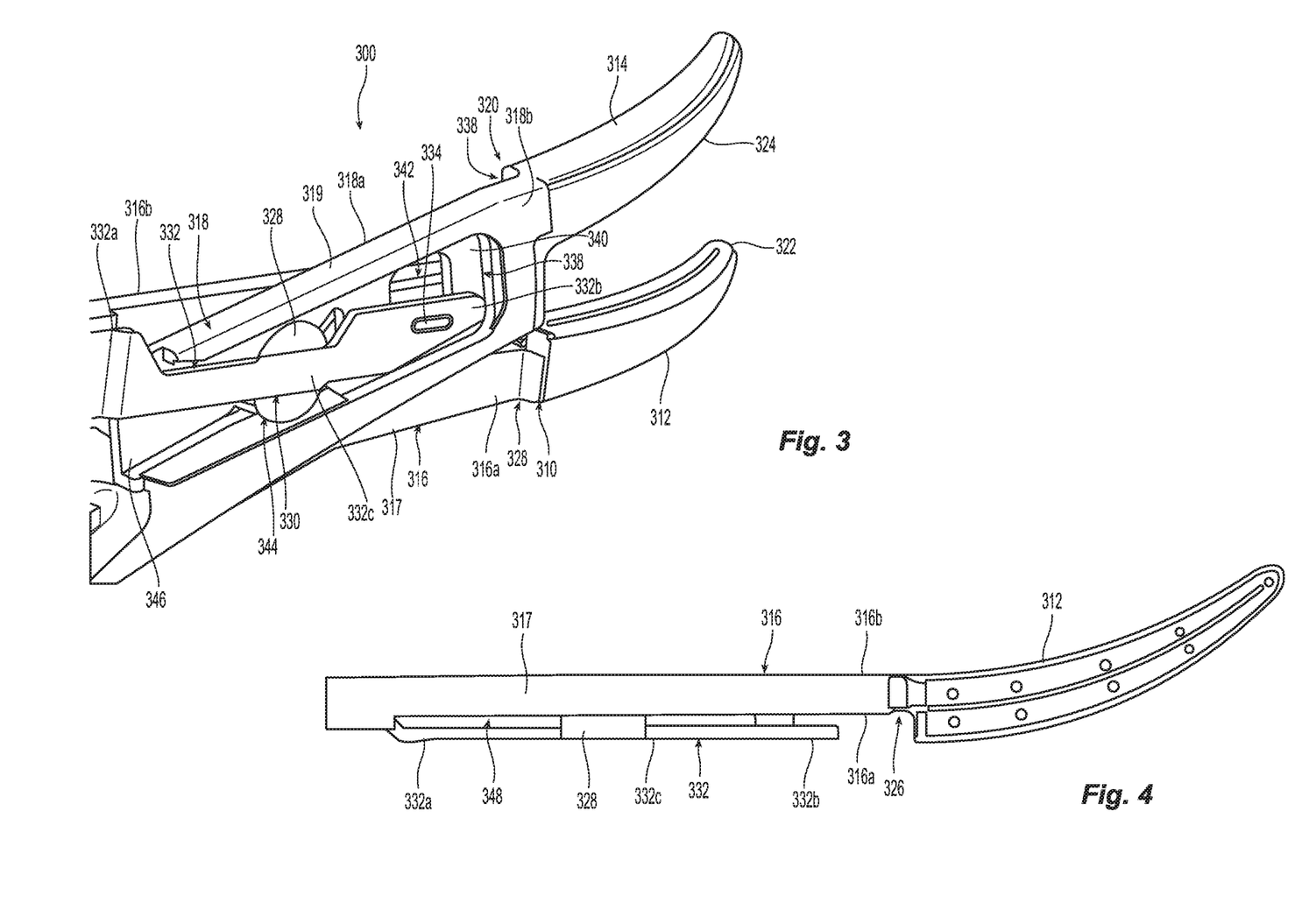
FIG. 3 is a side, perspective view of an exemplary embodiment of an end effector of an electrosurgical forceps.
FIG. 4 is a top view of a first jaw member of the end effector shown in FIG. 3.

With reference to FIGS. 3 and 4, another embodiment of an end effector 300 is illustrated, which is configured to replace end effector 200 of electrosurgical forceps 100 (FIGS. 1 and 2). In particular, end effector 300 includes first and second jaw members 310, 320 configured to be coupled to distal end portions 112b, 122b (FIGS. 1 and 2) of first and second shaft members 110, 120, respectively. In embodiments, first and second jaw members 310, 320 of end effector 300 may be welded to, monolithically formed with, or otherwise engaged to inner frames 114, 124 of first and second shaft members 110, 120, respectively.

Each of the first and second jaw members 310, 320 has a jaw body 312, 314 and a proximal body portion 316, 318 extending proximally from the jaw body 312, 314. First and second jaw bodies 312, 314 and first and second proximal body portions 316, 318 are monolithically formed with one another. In other embodiments, first and second jaw bodies 312, 314 and first and second proximal body portions 316, 318 may be fastened to one another. First and second jaw members 310, 320 each have a tissue-sealing plate 322, 324 supported on the respective first and second jaw bodies 312, 314. Sealing plates 322, 324 are in electrical communication with an electrosurgical generator via electrosurgical cable 160 (FIG. 2).

First and second proximal body portions 316, 318 of first and second jaw members 310, 320 are coupled to (e.g., formed with or connected to) distal end portions 112b, 122b (FIGS. 1 and 2) of first and second shaft members 110, 120.

First proximal body portion 316 of first jaw member 310 may have a substantially flat, rectangular shape. In aspects, first proximal body portion 316 may assume any suitable shape. First proximal body portion 316 has a segment 317 having a reduced width that is less than a width of first jaw body 312. Consequently, segment 317 has a recess 326 for receiving second proximal body portion 318 of second jaw member 320.

First proximal body portion 316 has an inner lateral side 316a and an opposite, outer lateral side 316b. First jaw member 310 has a pivot pin 328 extending laterally from inner lateral side 316a and is rotationally fixed relative to first proximal body portion 316. In aspects, pivot pin 328 may be monolithically formed with first proximal body portion 316. Pivot pin 328 defines a longitudinally-extending slot 330 dimensioned for receipt of a portion of a cap 332 of end effector 300. First proximal body portion 316 further includes a protuberance 334 extending laterally from inner lateral side 316a for fixation with cap 332, as will be described.

Second proximal body portion 318 of second jaw member 320 has an inner lateral side 318a and an opposite, outer lateral side 318b. Inner lateral side 318a of second proximal body portion 318 faces and is disposed adjacent inner lateral side 316a of first proximal body portion 316. Second proximal body portion 318 has a segment 319 having a reduced width that is less than a width of second jaw body 320. Consequently, segment 319 of second jaw member 320 has a recess 336 for receiving segment 317 of first jaw member 310, such that upon segments 317, 319 of first and second jaw members 310, 320 being received in the corresponding recesses 336, 326 of the second and first jaw members 320, 310, the outer periphery of the first and second proximal body portions 316, 318 are streamlined with the outer periphery of the first and second jaw bodies 312, 314.

Second proximal body portion 318 of second jaw member 320 defines a recessed cavity 338 in outer lateral side 318b thereof. Second proximal body portion 318 has an inner surface 340 disposed at a bottom of recessed cavity 338. Inner surface 340 defines an opening 342 transversely therethrough having protuberance 334 of first proximal body portion 316 extending therethrough. Second proximal body portion 318 defines a cylindrical bore 344 transversely therethrough. Pivot pin 328 of first jaw member 310 extends through cylindrical bore 344 of second jaw member 320 to support second jaw member 320 relative to first jaw member 310. Cylindrical bore 344 is sized to allow second jaw member 320 to pivot about and relative to pivot pin 328.

Cap 332 of end effector 300 is received in recessed cavity 338 of second proximal body portion 318 and fixed to inner lateral side 316a of first proximal body portion 316 to retain first and second jaw members 310, 320 to one another without inhibiting second jaw member 320 from pivoting relative to pivot pin 328 of first jaw member 310. Cap 332 may be an elongated plate-like structure having a proximal end portion 332a, a distal end portion 332b, and an intermediate portion 332c therebetween. Distal end portion 332b of cap 332 is in abutment with inner surface 340 of second proximal end portion 318 and welded to protuberance 334 of first jaw member 310. Intermediate portion 332c of cap 332 is captured in slot 330 of pivot pin 328 (e.g., via friction-fit) and welded thereto. Proximal end portion 332a of cap 332 extends proximally from an open proximal end 346 of recessed cavity 338 of second proximal body portion 318 and is welded to inner lateral side 316a of first proximal body portion 316. In other embodiments, various locations of cap 332 may be welded or otherwise fixed to first jaw member 310 (e.g., glued, friction-fit, fastened).

With cap 332 welded or otherwise fixed to first jaw member 310 and cap 332 abutting outer lateral side 318b of second jaw member 320, second jaw member 320 is retained with first jaw member 310 while remaining pivotable in relation to and about pivot pin 328 of first jaw member 310. As best shown in FIG. 4, cap 332 is spaced from inner lateral side 316a of first proximal body portion 316 to define a gap 348 between cap 332 and inner lateral side 316a of first proximal body portion 316. Inner surface 340 (FIG. 3) of second proximal body portion 318 is disposed in gap 348 to form a lockbox configuration with first proximal body portion 316.

Figure 5:
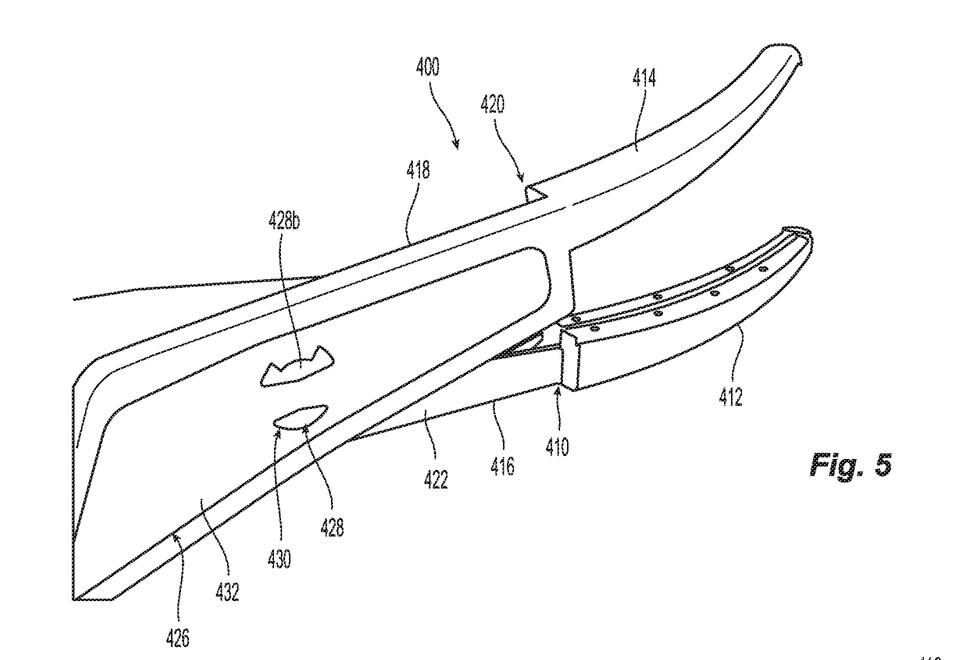
FIG. 5 is a side, perspective view of another embodiment of an end effector of an electrosurgical forceps.
Figure 6:
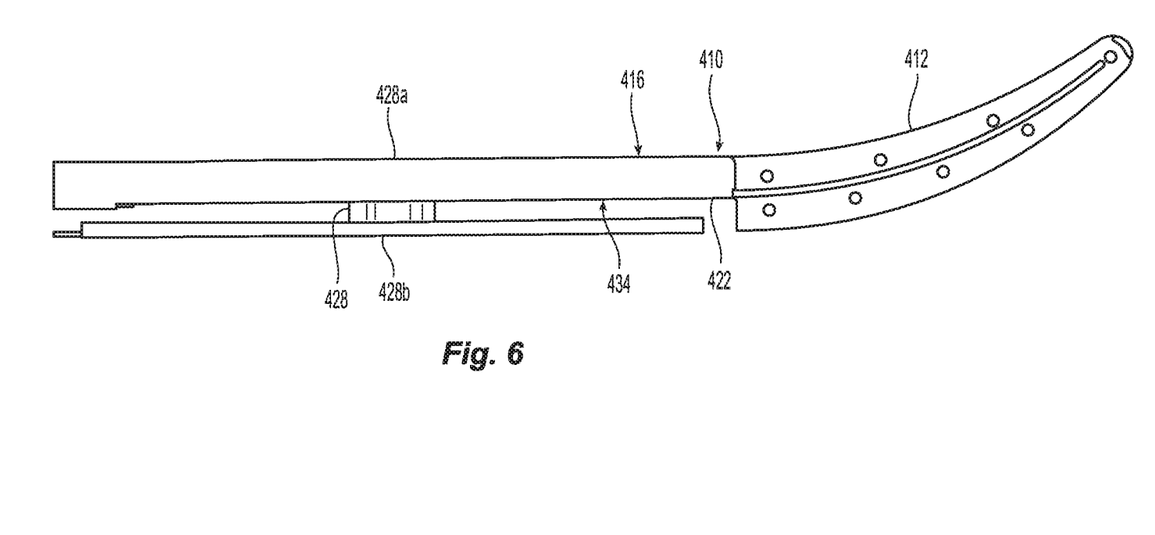
FIG. 6 is a top view of a first jaw member of the end effector shown in FIG. 5.

With reference to FIGS. 5 and 6, another embodiment of an end effector 400 is illustrated, similar to end effector 300 described above. Accordingly, end effector 400 will only be described to the extent believed necessary in elucidating its differences from end effector 300. End effector 400 includes first and second jaw members 410, 420 configured to be coupled to distal end portions 112b, 122b (FIGS. 1 and 2) of first and second shaft members 110, 120, respectively. In embodiments, first and second jaw members 410, 420 of end effector 400 may be welded to, monolithically formed with, or otherwise engaged to inner frames 114, 124 of first and second shaft members 110, 120, respectively.

Each of the first and second jaw members 410, 420 has a jaw body 412, 414, and a proximal body portion 416, 418 extending proximally from the jaw body 412, 414. First proximal body portion 416 of first jaw member 410 has an inner lateral side 422. First proximal body portion 416 defines a hole (not explicitly shown) transversely therethrough. End effector 400 further includes a pivot pin 428 having a first end 428a received in the hole of first proximal body portion 416. First end 428a of pivot pin 428 is retained with first proximal body portion 416 while being permitted to rotate within the hole.

Second proximal body portion 418 of second jaw member 420 has an inner lateral side 424 facing and disposed adjacent inner lateral side 422 of first proximal body portion 416. Second proximal body portion 418 defines a cavity 426 therein dimensioned for receipt of a cap 432 of end effector 400. Cap 432 may be received in cavity 426, such that an outer surface of cap 432 is flush with an outer lateral side of second proximal body portion 418. Cap 432 defines an opening or openings 430 for receiving a second end 428b of pivot pin 428. With second end 428b of pivot pin 428 received in openings 430 of cap 428, and cap 4328 received in cavity 426 of second proximal body portion 418, cap 428 is welded to second end 428b of pivot pin 428 and second proximal body portion 418. In other embodiments, cap 432 may be fixed to pivot pin 428 and second proximal body portion 418 using any suitable fastening engagement, such as, for example, friction-fit, adhesive, or the like.

After cap 432 is welded or otherwise fixed to second jaw member 420 and second end 428b of pivot pin 428, first and second jaw members 410, 420 are retained to one another while remaining pivotable in relation to one another. As best shown in FIG. 6, cap 432 is spaced from inner lateral side 422 of first proximal body portion 416 to define a gap 434 between cap 432 and inner lateral side 422 of first proximal body portion 416. Second proximal body portion 418 is disposed in gap 434 to form a lockbox configuration with first proximal body portion 416.

Figure 7:
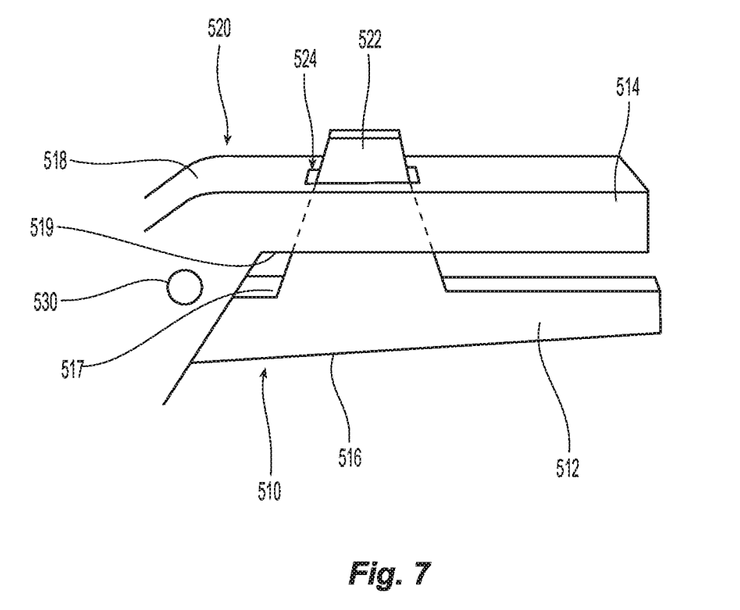
FIG. 7 is a side, perspective view of yet another embodiment of an end effector of an electrosurgical forceps.

With reference to FIG. 7, another embodiment of an end effector 500 is illustrated, similar to end effector 200 described above. Accordingly, end effector 500 will only be described to the extent believed necessary in elucidating its differences from end effector 200. End effector 500 includes first and second jaw members 510, 520 configured to be coupled to distal end portions 112b, 122b (FIGS. 1 and 2) of first and second shaft members 110, 120, respectively. In embodiments, first and second jaw members 510, 520 of end effector 500 may be welded to, monolithically formed with, or otherwise engaged to inner frames 114, 124 of first and second shaft members 110, 120, respectively.

Each of the first and second jaw members 510, 520 has a jaw body 512, 514, and a proximal body portion 516, 518 extending proximally from the jaw body 512, 514. Rather than being disposed side-by-side, first and second proximal body portions 516, 518 overlap one another, such that an upper surface 517 of first proximal body portion 516 and a lower surface 519 of second proximal body portion 518 face one another.

First proximal body portion 516 of first jaw member 510 has a tooth 522 projecting laterally from upper surface 517 thereof toward lower surface 519 of second jaw member 520. Tooth 522 may assume any suitable shape, such as, for example, trapezoidal, square, cylindrical, or the like. Second proximal body portion 518 of second jaw member 520 has an open window 524 defined therethrough. Tooth 522 of first jaw member 510 remains disposed within open window 524 of second jaw member 520 throughout movement of first and second jaw members 510, 520 between approximated and open positions. The receipt of tooth 522 in open window 524 prevents relative lateral movement of first and second jaw members 510, 520 while allowing first and second jaw members 510, 520 to pivot about a pivot member 530.

For a detailed description of various components and manners of operating forceps 100 of the present disclosure, reference may be made to U.S. Publication No. US 2018-0325580 A1, the entire contents of which are incorporated by reference herein.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector of an electrosurgical forceps, comprising:
    a first jaw member including:
        a jaw body; and
        a proximal body portion extending proximally from the jaw body and having an inner lateral side and a pivot pin extending inwardly from the inner lateral side;
    a second jaw member including:
        a jaw body; and
        a proximal body portion extending proximally from the jaw body of the second jaw member and pivotably coupled to the pivot pin, the proximal body portion of the second jaw member having an inner lateral side adjacent the inner lateral side of the first jaw member; and
    a cap fixed to the inner lateral side of the proximal body portion of the first jaw member and coupling the first and second jaw members to one another, wherein the cap and the pivot pin are non-rotationally fixed to the first jaw member,
    wherein the proximal body portion of the second jaw member defines an opening extending laterally therethrough, the proximal body portion of the first jaw member having a protuberance projecting from the inner lateral side thereof and through the opening, the cap having a distal end portion fixed to the protuberance.

2. The end effector according to claim 1, wherein the pivot pin defines a slot having a portion of the cap received therein.

3. The end effector according to claim 1, wherein the cap has a proximal end portion and a distal end portion, the proximal and distal end portions of the cap fixed to the proximal body portion of the first jaw member.

4. The end effector according to claim 2, wherein the cap has an intermediate portion received in the slot of the pivot pin.

5. The end effector according to claim 1, wherein the proximal body portion of the second jaw member defines a recessed cavity configured to receive the cap therein.

6. The end effector according to claim 5, wherein the proximal body portion of the second jaw member has an inner surface disposed in the recessed cavity, the cap disposed over and in contact with the inner surface.

7. The end effector according to claim 1, wherein the pivot pin is fixed relative to the proximal body portion of the first jaw member.

8. The end effector according to claim 1, wherein the cap is welded at the proximal and distal end portions to the inner lateral side of the first jaw member.

9. The end effector according to claim 1, wherein the cap is spaced laterally from the inner lateral side of the first jaw member to define a gap between the cap and the inner lateral side of the first jaw member, the gap configured to receive the proximal body portion of the second jaw member therein.

* * * * *